United States Patent
Maschke

(10) Patent No.: US 8,095,201 B2
(45) Date of Patent: Jan. 10, 2012

(54) MEDICAL DEVICE AND METHOD FOR OPERATING A MEDICAL DEVICE

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 610 days.

(21) Appl. No.: 12/231,659

(22) Filed: Sep. 4, 2008

(65) Prior Publication Data

US 2009/0069660 A1 Mar. 12, 2009

(30) Foreign Application Priority Data

Sep. 10, 2007 (DE) .................. 10 2007 042 986

(51) Int. Cl.
*A61B 5/05* (2006.01)

(52) U.S. Cl. ......... 600/407; 600/411; 422/102; 378/210

(58) Field of Classification Search .................. None
See application file for complete search history.

(56) References Cited

U.S. PATENT DOCUMENTS

| 5,632,957 | A * | 5/1997 | Heller et al. ............... 506/39 |
| 5,835,558 | A | 11/1998 | Maschke |
| 6,382,835 | B2 | 5/2002 | Graumann et al. |
| 6,534,323 | B1 * | 3/2003 | Sabbadini ................ 436/518 |
| 6,602,855 | B2 | 8/2003 | Digby et al. |
| 2002/0127740 | A1 * | 9/2002 | Ho .......................... 436/518 |
| 2002/0160434 | A1 | 10/2002 | Jackowski et al. |
| 2004/0146874 | A1 * | 7/2004 | Inami et al. ................ 435/6 |
| 2005/0101841 | A9 * | 5/2005 | Kaylor et al. .............. 600/300 |
| 2005/0130226 | A1 | 6/2005 | Ahn et al. |
| 2005/0136496 | A1 | 6/2005 | Jackowski |
| 2005/0153379 | A1 | 7/2005 | Hoon et al. |
| 2007/0219366 | A1 | 9/2007 | Gumbrecht et al. |
| 2008/0031503 | A1 * | 2/2008 | Kanada et al. ............. 382/128 |
| 2008/0154342 | A1 * | 6/2008 | Digby et al. ............... 607/63 |
| 2008/0241890 | A1 | 10/2008 | Gumbrecht et al. |
| 2009/0312638 | A1 * | 12/2009 | Bartlett ..................... 600/443 |

FOREIGN PATENT DOCUMENTS

| DE | 4436828 C1 | 3/1996 |
| DE | 196 27 657 C2 | 1/2003 |
| DE | 102004021780 A1 | 11/2005 |
| DE | 102004021822 B3 | 11/2005 |
| DE | 600 16 178 T2 | 12/2005 |
| DE | 100 03 524 B4 | 7/2006 |
| WO | WO2008009044 * | 1/2008 |

OTHER PUBLICATIONS

Mobilett XP CR Flyer; Others; 2006.

* cited by examiner

*Primary Examiner* — Brian Casler
*Assistant Examiner* — Saurel J Selkin

(57) ABSTRACT

The possibility for receiving and processing data from an analytical chip ("lab-on-a-chip") is integrated into a medical device, such as for example an X-ray imaging system. This means quite simply that it is possible at the medical device to make a diagnosis which could otherwise only be made by a laboratory. There is a separate processor unit, a separate memory a separate input/output unit, adapted to the analytical chip, and a display unit displays both image data from the X-ray imaging system and also analytical data.

13 Claims, 2 Drawing Sheets

MEDICAL DEVICE AND METHOD FOR OPERATING A MEDICAL DEVICE

CROSS REFERENCE TO RELATED APPLICATIONS

This application claims priority of German application No. 10 2007 042 986.1 filed Sep. 10, 2007, which is incorporated by reference herein in its entirety.

FIELD OF THE INVENTION

The invention relates to a medical device with a main unit which serves directly to obtain image data or for therapy on a patient, and with a data processing facility for processing data for or from the main unit.

The above definition covers a host of diagnostic or therapeutic devices.

BACKGROUND OF THE INVENTION

The image recording devices include X-ray imaging systems of various types, from a simple through-illumination system through angiographic devices to computer tomographs. The image recording devices include also PET devices (where PET stands for positron emission tomography) and SPECT devices (where SPECT stands for single photon emission computer tomography). Medical devices of the generic type mentioned in the introduction can also include magnetic resonance devices. The device can also work with ultrasound. Finally, optical endoscopes and equipment for optical coherence tomography also belong with the devices cited above. When the above medical device is designed as a therapeutic device, it may incorporate a linear accelerator or proton therapy equipment.

Medical devices of the generic type cited are normally so large that the patient is brought to the device, and not the device to the patient. Frequently, the medical device fills the treatment room into which the patient is brought. With the help of an imaging device it is possible to obtain pictures of bones, vessels and organs. When designed as a therapeutic device, treatment is carried out on the patient. In both cases it is generally important that a reliable diagnosis can be made for the patient, that is the patient's illness or injury, as applicable, can be clearly identified. Frequently, the making of a diagnosis requires an analysis of bodily fluids. This is usually carried out somewhere away from the medical device. In a hospital environment, the bodily fluid is taken, for example, to a separate hospital laboratory, there it is analyzed and the result is reported back. In particular in the case of emergency patients, this is a bad thing, because time is lost due to the long distances and the awkwardness of the procedure.

The publication US 2005/0153379 A1 describes a measuring probe with which an analytical chip can be introduced into a patient's bloodstream. Using such a measuring probe, the in vivo detection of tumor cells and similar biological markers is possible. The concentration of the biological markers, measured using the chip, can be read out via the probe and shown on a display device. Instead of a chip, the measuring probe can also have two glass fibers, where light is conducted to the tip of the measuring probe via one of the glass fibers and the light reflected by the bodily fluids is fed back via the second glass fiber. Using a spectral analysis of the reflected light, it is again possible to draw conclusions about the presence of certain biological markers.

SUMMARY OF THE INVENTION

It is the objective of the invention to enable faster treatment of the patient, in particular also by a speeded-up diagnosis of bodily fluids.

This objective is achieved in that the medical device's data processing facility is arranged to receive and process data obtained with the help of an analytical chip.

Analytical chips, also frequently referred to as a "lab-on-a-chip", are credit-card sized systems, to which a bodily fluid or a bodily tissue can be fed, where a reaction takes place on the system and a result can be read out, normally with the help of an analytical chip holder into which the analytical chip is inserted. The analytical chip holder offers the ability to read data out from the analytical chip.

Because of the fact that the medical device's data processing facility is now, in accordance with the invention, arranged to receive and process the data from the analytical chip, the convenient laboratory system is an integral part of the medical device's environment. Even in itself, an analytical chip has numerous advantages, namely in particular that an analysis is available within a short time, and this at a site remote from the laboratory. This advantage is now exploited in a positive way in conjunction with the medical device which, with its data processing facility, provides the electronics required for the evaluation of the data obtained by the analytical chip, so that there is no longer a need for the separate provision of this.

On the spot analysis with the help of an analytical chip can in particular give information about the proportion of blood gases in the patient's blood, the proportion of blood sugar, the composition of the patient's blood corpuscles and about clotting factors. The blood can also be analyzed in respect of certain enzyme markers, which give an indication of an acute cardiac infarction which has taken place. These include, for example, the total creatine phosphokinase (CPK), troponin and B-type protein and myoglobin. There are also more recent so-called cardiac markers, which give an indication of a cardiac infarction, and of the numerous cardiac markers we mention here myeloperoxidase (MPO) and brain natriuretic peptide (BNP), c.f. also the biopolymer markers cited in U.S. Pat. No. 6,602,855 B2.

Using an analytical chip it is also possible to investigate the blood for markers which indicate a stroke. These include the serum phosphoglycerate mutase B-type isozyme, the B-type neurotropic growth factor, a biopolymer marker which is described in U.S. Pat. No. 6,602,855 B2, a combination marker comprising four sub-markers which is described in DE 600 16 178 T2, and many others.

With the help of the analytical chip it is thus possible to make an on-site determination within a short time as to whether the patient should be investigated for something particular, such as for example a cardiac infarction or a stroke. By its diagnostic result, the analytical chip helps directly with the further investigation of the patient with the help of the medical device which receives and processes the result of the analysis. This raises the overall efficiency in the diagnosis and treatment of the patient.

An analytical chip holder can be permanently integrated into the medical device: it must then be (permanently) connected to a data bus which carries data from and to the data processing facility. An analytical chip can be accommodated in the analytical chip holder and, with the help of the holder, data can be read out from the analytical chip it is accommodating.

The form of embodiment with the integrated analytical chip holder has the advantage that it can have a very compact construction, and operating staff can put the medical device into operational readiness especially quickly when a diagnosis is wanted.

In the case of an alternative form of embodiment, use is made of a variety of device modules. The analytical chip holder is then only one of several device modules. There is then naturally an interface to the medical device's data bus for the analytical chip holder. This form of embodiment has the advantage that not every device of the same model has an analytical chip holder, which may possibly prove to be superfluous in the specific instance. In particular, analytical chip holders can be saved if there are several medical devices in the immediate neighborhood of each other. It is then sufficient to equip only one of the medical devices with an analytical chip holder.

It is not a requirement of the invention that the data obtained with the help of the analytical chip should be available exclusively in the medical device or its data processing facility, as applicable. So the device (and in particular the data processing facility) can incorporate facilities for reading the data, obtained with the help of the analytical chip, into a data transmission network. It is conceivable, for example, that the device feeds the data into a receiver which is present in the building, which routes the data to a central computer via a cabling system. These facilities for reading-in are not straightforward to provide, even on analytical chip holders which are easy to transport, e.g. are portable. The medical device in accordance with the invention thus makes use of synergistic effects and also offers advantages compared with the prior art, over and above the application of the diagnostic date within the device itself.

Although the medical device can be statically located, it is however entirely possible that it can be manually moved as a whole, e.g. it is drivable. This is already a known situation, in particular for X-ray devices and ultrasound devices. For example, a drivable X-ray device is described in DE 100 03 524 B4 or also in DE 196 27 657 C2.

Something is then already gained over the prior art by the invention, if the doctor managing the treatment can access the data processing facility, can look on a screen at the data obtained by the analytical chip after it has been processed to make it suitable for display and then, on the basis of the diagnosis, can make a decision about how to proceed in operating the medical device. With one preferred form of embodiment of the invention, this decision is even made automatically. The medical device then incorporates a controller which is arranged to put the main unit into either a first mode or another mode, depending on whether or not the data which has been received, and preferably has already been processed, fulfills a predefined criterion. As an example, simple threshold value criteria can be used. If there is a suspicion of a cardiac infarction, use can be made of an analytical chip which gives information about the presence in the blood of certain cardiac markers. If the threshold value is exceeded, it is certain that a cardiac infarction has occurred, and the medical device can automatically work in a mode which is adjusted for a diagnosis of "cardiac infarction". For example, an X-ray imaging device can automatically be given certain presettings, e.g. those concerning the positioning of the X-ray radiation source and X-ray detector, the X-ray radiation dose, the sensitivity of the detector etc.

An additional aspect of the present invention is a method for operating a medical device of the type in accordance with the invention, to which an analytical chip holder can be coupled or already is coupled. A controller enables the main unit to be operated in at least two different modes. The method includes the following steps:

a) couple an analytical chip to the data bus via a/the analytical chip holder (this may include the coupling of the analytical chip holder if it is not already coupled with the device),
b) feed a sample (fluid, tissue sample) which is to be analyzed to the analysis chip,
c) read out an analysis result with the help of the analytical chip holder and feed this to the data processing facility,
d) if the result of the analysis satisfies a predefined criterion, (automatically) arrange for the controller to work in a first mode, and
if the analytical device does not satisfy the predefined criterion, (automatically) arrange for the controller to work in a second mode.

The advantages of the method in accordance with the invention have already been mentioned above, in the discussion of the last preferred form of embodiment of the medical device which was cited.

BRIEF DESCRIPTION OF THE DRAWINGS

Preferred forms of embodiment of the invention are described below with reference to the drawing, in which.

DETAILED DESCRIPTION OF THE INVENTION

Figure 1:
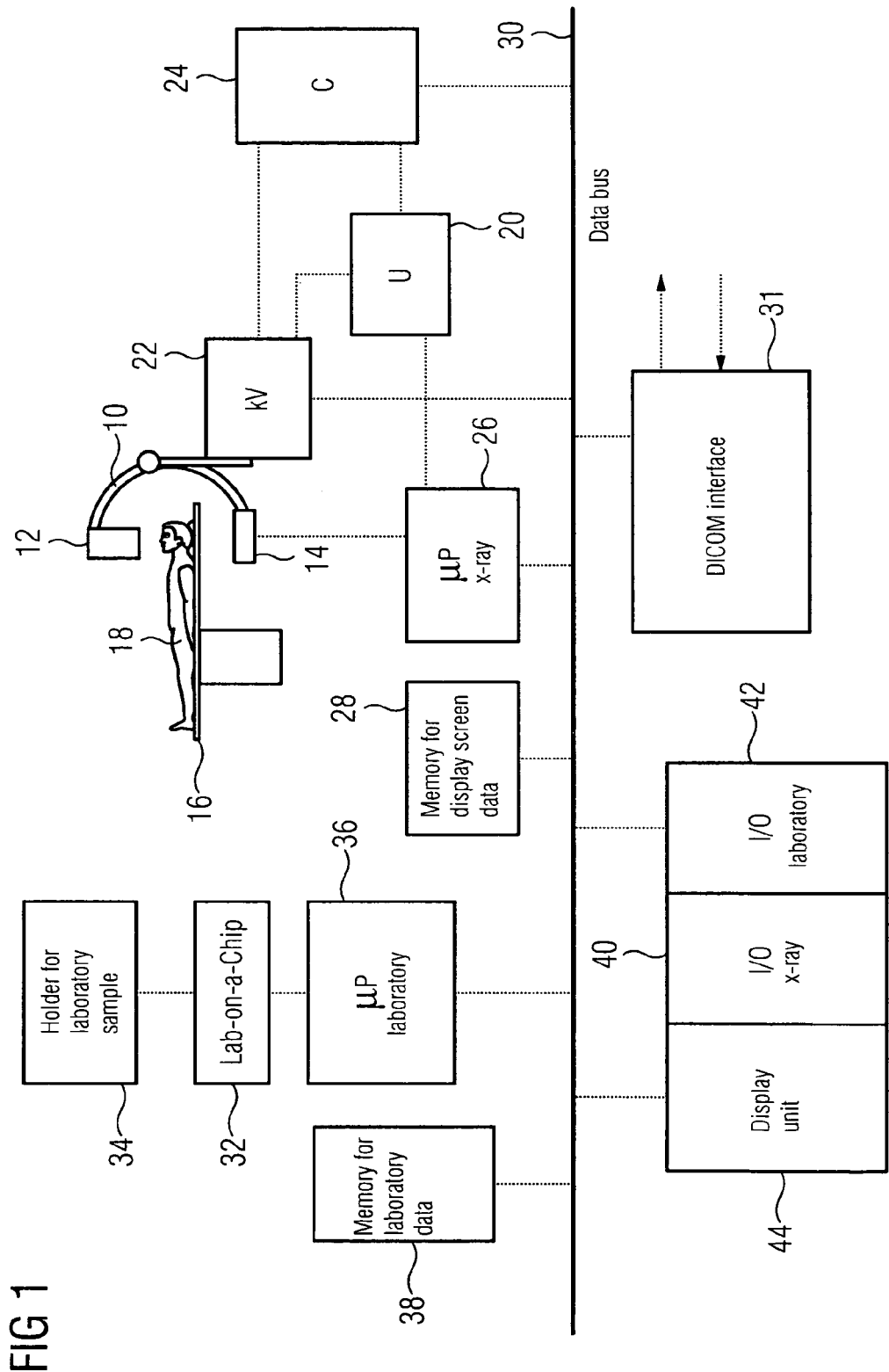
FIG. 1 shows a schematic of the structure of an X-ray imaging system in accordance with the invention.

The example explained below, of a medical device of a type in accordance with the invention, is an X-ray imaging system. The heart of the X-ray imaging system is a X-ray C-arm 10 with an X-ray radiation source 12 and an X-ray detector 14, which are used for imaging a patient 18 lying on a patient table 16. A power supply 20 supplies all the units with power, where required. A high voltage generator 22 generates the high voltage required for the X-ray radiation source 12. A system controller 24 controls the entire X-ray imaging system. A processor unit "X-ray processor unit" 26 processes the X-ray images recorded by the X-ray detector 14. The images recorded together also with the associated data are stored away in a memory 28. The individual units communicate with each other via a data bus 30. Connected to this data bus 30 is a DICOM interface 31, via which the data and images for the patient can be exchanged with other devices, e.g. image data obtained before the current treatment.

The data bus 30 is now used in addition for data obtained with the help of an analytical chip 32 ("lab-on-a-chip"). For this purpose, an analytical chip holder is connected to the data bus (not shown). What is shown schematically is that an analytical chip 32 is provided, to which a laboratory sample can be fed via a holder 34. A processor unit, which can be part of the analytical chip holder mentioned and in FIG. 1 is called the "Laboratory processor unit" and is labeled 36, processes the data obtained with the help of the analytical chip 32. The data thus obtained is stored away in the memory 38. The data processing facility of the medical device shown in FIG. 1 thus consists of the processor unit 26 and the processor unit 36. The processor units can also be combined into one single processor unit. What is important is the direct connection of the analytical chip 32 to the data bus 30, that is the direct connection of the processor unit 36 to it. Then there is also a user interface. The user can input data connected with the operation of the X-ray C-arm 10, or more generally with the X-ray equipment overall, via an input/output unit 40. The user can input data, which is in some way to do with the analysis by the analytical chip 32, via a second input/output unit 42. A display unit 44 shows X-ray images and analysis data consecutively or simultaneously.

The medical device shown in FIG. 1 is in no way produced by merely connecting the analytical chip 32 to a conventional X-ray device. Rather, it is specially arranged to control and read-out the analytical chip 32, as can be seen from the user interface with the input/output unit 42 and also by the fact that the display unit 44 does not treat the data from the analytical chip 32 as external data but as data which naturally belongs to the present device.

Figure 2:
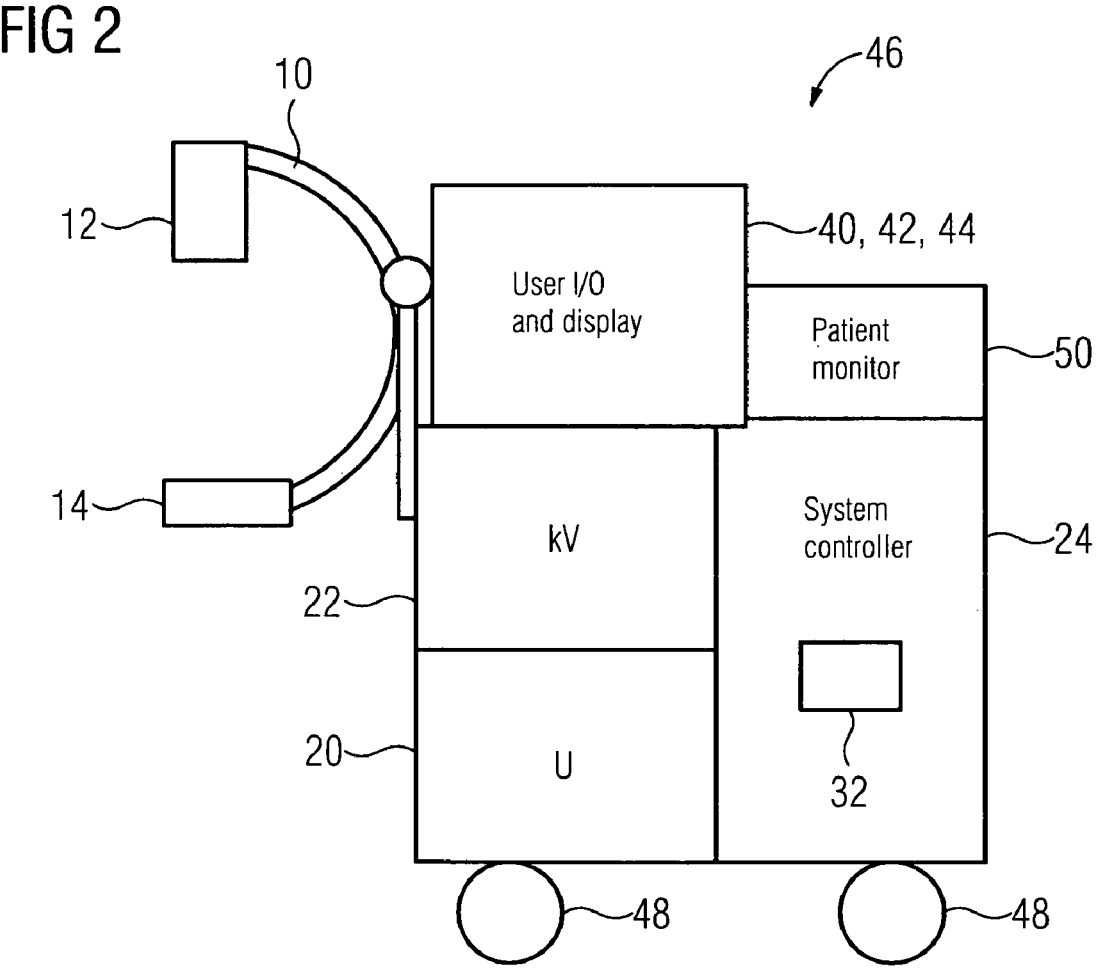
FIG. 2 shows a moveable X-ray imaging system of the type in accordance with the invention.

FIG. 2 shows a derivative of the medical device in FIG. 1. The medical device (X-ray imaging device) in FIG. 2, which as a whole is labeled 46, is now drivable in that the individual subassemblies are on rollers 48. The construction of the X-ray imaging system 46 in FIG. 2 is essentially no different from the medical device in FIG. 1, so that subassemblies which are the same are also labeled with the same reference numbers, where some of the units in FIG. 1 have been chosen by way of example. In addition, a so-called patient monitor 50 is provided, which makes possible an analysis of the data appropriate for the patient.

In the case of both forms of embodiment it is possible, with the help of the analytical chip 32, to investigate a laboratory sample, e.g. with blood from the patient 18, for known markers such as troponin and myoglobin or even for the cardiac markers which have more recently become known, C-reactive protein (CRP), and brain natriuretic peptide (BNP), and indeed in accordance with the methods cited in US 2005/0130226 A1. It thereby becomes very quickly clear whether or not the patient 18 has suffered a heart infarction, that is the diagnosis is available in at short notice. The system controller 24 can be controlled by the doctor, or even automatically, in such a way that X-ray images are recorded which are appropriate for the diagnosis.

The invention claimed is:

1. A medical device, comprising:
an imaging device configured to obtain image data of a patient;
a data processing unit that receives and processes the image data; and
an analytical chip configured to analyze one of a bodily fluid sample and a bodily tissue sample of the patient, said analytical chip is connected to the data processing unit to provide a result of the analysis to the data processing unit;
wherein said data processing unit is configured to process the image data based on the result of the analysis of the analytical chip,
wherein the imaging device is an X-ray imaging device including an X-ray source and an X-ray detector; said X-ray source and said X-ray detector are configured to obtain X-ray image data of the patient;
and wherein the data processing unit is configured to adjust a position of at least one of the X-ray source and the X-ray detector based on the result of the analysis.

2. The medical device as claimed in claim 1, further comprising an analytical chip holder that accommodates the analytical chip.

3. The medical device as claimed in claim 2, wherein the image data and the result are transferred from and to the data processing unit via a data bus.

4. The medical device as claimed in claim 3, wherein the data bus is coupled to the analytical chip holder to read out the result from the analytical chip.

5. The medical device as claimed in claim 3, wherein the analytical chip holder is connected to the data bus via an interface to read out the result from the analytical chip.

6. The medical device as claimed in claim 1, wherein the analytical chip provides the result that is read into a transmission network data.

7. The medical device as claimed in claim 1, wherein the medical device is manually transported in an entirety.

8. The medical device as claimed in claim 1, further comprising a controller that sets the imaging device into different modes depending on whether or not a predefined criterion is satisfied by the result of the analysis.

9. The medical device as claimed in claim 1, wherein the imaging device is an X-ray imaging device including an X-ray source and an X-ray detector; said X-ray source and said X-ray detector are configured to obtain X-ray image data of the patient.

10. The medical device as claimed in claim 1, wherein the analytical chip result is configured to provide at least one of a proportion of blood gases in the patient's blood, a proportion of blood sugar in the patient's blood, and a composition of the patient's blood corpuscles.

11. The medical device as claimed in claim 1, wherein said result of the analysis provides a level of cardiac markers in the patient's blood, and wherein said data processing unit is configured to determine if a threshold value of cardiac markers are exceeded.

12. The medical device as claimed in claim 1, further comprising a display unit connected to the data processing unit, said display unit configured to simultaneously display the result of the analysis and the image data.

13. A method for operating a medical device, comprising:
obtaining image data of a patient; coupling an analytical chip to a data bus via a analytical chip holder;
feeding one of a bodily fluid sample and a bodily tissue sample of the patient to the analytical chip;
reading out an analysis result of the one of the bodily fluid sample and the bodily tissue sample from the analytical chip;
feeding the analysis result to a data processing unit; processing the image data based on the analysis result,
wherein the medical device is an X-ray imaging device including an X-ray source and an X-ray detector; said X-ray source and said X-ray detector are configured to obtain X-ray image data of the patient;
and adjusting a position of at least one of the X-ray source and the X-ray detector based on the analysis result.

* * * * *